US009921147B2

(12) United States Patent
Aubert et al.

(10) Patent No.: US 9,921,147 B2
(45) Date of Patent: Mar. 20, 2018

(54) METHOD FOR CHARACTERIZING A LIQUID SAMPLE CONTAINING PARTICLES

(71) Applicant: Commissariat A L'Energie Atomique et aux Energies Alternatives, Paris (FR)

(72) Inventors: Vivian Aubert, Grenoble (FR); Myriam-Laure Cubizolles, Corenc (FR); Cedric Poulain, Grenoble (FR); Maxime Huet, Grenoble (FR); David Rabaud, Grenoble (FR)

(73) Assignee: Commissariat A L'Energie Atomique et aux Energies Alternatives, Paris (FR)

( * ) Notice: Subject to any disclaimer, the term of this patent is extended or adjusted under 35 U.S.C. 154(b) by 0 days.

(21) Appl. No.: 15/460,329

(22) Filed: Mar. 16, 2017

(65) Prior Publication Data
US 2017/0268989 A1    Sep. 21, 2017

(30) Foreign Application Priority Data
Mar. 17, 2016 (FR) .................. 16 52263

(51) Int. Cl.
*G01N 21/17* (2006.01)
*G01N 1/44* (2006.01)
(Continued)

(52) U.S. Cl.
CPC ......... *G01N 21/1717* (2013.01); *G01N 1/44* (2013.01); *G01N 21/03* (2013.01); *G01N 21/51* (2013.01);
(Continued)

(58) Field of Classification Search
CPC .................. G01N 21/1717; G01N 21/03
See application file for complete search history.

(56) References Cited

U.S. PATENT DOCUMENTS

| 5,225,089 A * | 7/1993 | Benes .................. B01D 21/283 |
| | | 210/188 |
| 2007/0119239 A1* | 5/2007 | Priev ...................... G01N 15/06 |
| | | 73/61.75 |

(Continued)

FOREIGN PATENT DOCUMENTS

| EP | 1 875 203 B1 | 5/2011 |
| WO | WO 90/05008 A1 | 5/1990 |

(Continued)

OTHER PUBLICATIONS

French Preliminary Search Report dated Nov. 16, 2016 in French Application 16 52263, filed Mar. 17, 2016 ( with English Translation of categories of cited documents and written opinion).

*Primary Examiner* — Roy M Punnoose
(74) *Attorney, Agent, or Firm* — Oblon, McClelland, Maier & Neustadt, L.L.P.

(57) ABSTRACT

The invention is a method for characterizing a liquid sample, said liquid sample containing particles, the method comprising the following steps:
  a) illuminating said sample using a light source that is able to emit an incident light wave towards the sample;
  b) detecting, using a photodetector, a light wave transmitted by the sample thus illuminated;
  c) characterizing the sample depending on an intensity of the light wave detected by the photodetector.

The method comprises, prior to step c), applying an acoustic wave to the sample, said acoustic wave forming pressure nodes and pressure antinodes in the sample, so as to separate, in the latter, a poor portion, poor in particles, and rich portion, rich in particles, such that, in step c), the sample is characterized:
  either on the basis of the intensity of the light wave transmitted by the poor portion;
(Continued)

or on the basis of the intensity of the light wave transmitted by the rich portion.

16 Claims, 6 Drawing Sheets

(51) Int. Cl.
G01N 21/51 (2006.01)
G01N 33/49 (2006.01)
G01N 21/03 (2006.01)

(52) U.S. Cl.
CPC ..... *G01N 33/49* (2013.01); *G01N 2021/1723* (2013.01); *G01N 2021/1761* (2013.01)

(56) References Cited

U.S. PATENT DOCUMENTS

| | | |
|---|---|---|
| 2008/0198360 A1 | 8/2008 | Dosmann et al. |
| 2010/0279326 A1 | 11/2010 | Dosmann et al. |
| 2011/0102768 A1 | 5/2011 | Dosmann et al. |
| 2012/0086938 A1 | 4/2012 | Folkenberg |
| 2014/0008307 A1* | 1/2014 | Guldiken .......... B01L 3/502761 210/748.05 |

FOREIGN PATENT DOCUMENTS

| | | |
|---|---|---|
| WO | WO 94/20833 A1 | 9/1994 |
| WO | WO 2011/006525 A1 | 1/2011 |

* cited by examiner

METHOD FOR CHARACTERIZING A LIQUID SAMPLE CONTAINING PARTICLES

FIELD OF THE INVENTION

The technical field of the invention is the optical analysis of a liquid containing particles, the optical analysis being coupled to a segmentation of the liquid into a phase rich in particles and a phase poor in particles.

BACKGROUND

Blood glucose level measurements are commonly taken using portable measuring devices in what are called point-of-care applications i.e. applications in which the measurements are taken at the patient's bedside or in the patient's home. This type of measurement may be taken by an optical method implementing an enzymatic reaction leading to the formation of a coloured indicator, for example a reaction based on a tetrazolium salt. A blood sample is then placed between a light source and a photodetector, the latter measuring an intensity of the light transmitted by the sample. However, the haematocrit level in the blood may have an influence on the measurement. Specifically, blood particles, in particular red blood cells, scatter and/or absorb the light passing through the sample, and it is necessary to take into account this perturbation.

A first way of allowing for the effect of the particles is to carry out, prior to the measurement, a haemolysis. This is what is described in patent U.S. Pat. No. 5,866,349. In this patent, an optical method for determining the concentration of glucose in whole blood is described. After a haemolysis step, the method implements the aforementioned enzymatic reaction. However, the haemolysis step may have certain drawbacks: on the one hand, it is an additional step, requiring a lysis reagent be added and a time be waited for the amount of lysed particles to be sufficient. On the other hand, as indicated in patent application EP1875203, the particle lysis may release, into the blood plasma, intracellular components that are liable to react with the coloured indicator. Thus, the lysis step adds complexity and may have an impact on the precision of the measurement.

There are alternatives to haemolysis. For example, patent EP1875203 describes a device allowing an amount of glucose in a blood sample to be estimated without implementation of haemolysis. The measuring principle is also based on the formation of a coloured indicator via reduction of a tetrazolium salt. The blood sample is coupled to the photodetector by two lenses that are placed in succession between the sample and the photodetector. These lenses allow the signal collected by the photodetector to be increased. The photodetector may be a CCD photodetector matrix array. Two light sources are used, one emitting in a spectral band of absorption of the coloured indicator, the other emitting in the near infrared. The detection of the light radiation transmitted by the sample, illuminated in the infrared, allows a haematocrit level to be determined and the detection of the light radiation transmitted by the sample in the spectral band of absorption of the indicator allows an amount of glucose to be estimated, this estimation being corrected for the haematocrit level determined beforehand. However, the implementation of a complex optical system based on two hemispherical lenses negatively affects the compactness of the device and its cost.

More generally, apart from blood, the analysis of a liquid containing particles may pose problems related to the presence of said particles. Known methods employ centrifugation of the sample to achieve an effective separation of the particles. However, centrifugation is a technique that is not easily integrable into a point-of-care type device. It requires the use of moving parts and powerful actuators. It may also lead to a lysis of certain particles.

The proposed invention addresses this problem, by providing a simple method allowing a characterization of a liquid containing particles to be obtained. The invention may be implemented using a simple and inexpensive device requiring neither a complex optical system nor successive illumination of the sample at two different wavelengths.

SUMMARY

A first subject of the invention is a method for characterizing a sample, including a liquid medium containing particles, the method comprising the following steps:
  a) illuminating the sample using a light source that is able to emit an incident light wave that propagates towards the sample;
  b) detecting, using a photodetector, a light wave transmitted by the sample thus illuminated;
  c) characterizing the sample depending on a intensity of the light wave detected by the photodetector;
the method comprising, prior to step b), a step of applying an acoustic wave to the sample, said acoustic wave forming pressure nodes and pressure antinodes in the sample, so as to separate, in the latter, a rich portion, also called enriched portion, and a poor portion, also called depleted portion, the concentration of particles being higher in the rich portion than in the poor portion, wherein step c) includes characterizing the liquid medium on the basis of the intensity of the light wave transmitted by the poor portion.

By transmitted light wave, what is meant is a light wave resulting from the illumination of the sample by the incident light wave, after the latter has passed through the sample. The terms pressure nodes and pressure antinodes designate those zones of the sample in which the amplitude of the acoustic pressure wave is minimal and maximal, respectively.

Under the effect of the acoustic wave, the particles present in the sample may concentrate either level with said pressure nodes, or level with said pressure antinodes.

By optical property, what is meant is the amount the sample absorbs or scatters in one or more spectral bands. It may be a question of a colour of the sample.

The characterization may comprise estimating a number of particles composing the sample, determining an optical property of the liquid medium in which the particles are contained, or determining how said optical property varies as a function of time.

According to an embodiment, the characterization comprises estimating an amount of an analyte in the liquid medium.

According to an embodiment, the method includes, prior to step b), mixing the sample with a reagent able to modify an optical property of the liquid medium under the effect of the analyte. The reagent can form a coloured indicator in the liquid medium, under the effect of the analyte.

The sample can include cells in a cellular culture medium, the coloured indicator being such that its colour changes depending on the pH of the culture medium.

The sample can include red blood cells in blood plasma, the coloured indicator being such that its colour changes depending on an amount of glucose in the plasma.

According to an embodiment, the photodetector is an image sensor, such that:

step b) comprises acquiring at least one image of the light wave transmitted by the sample;

step c) comprises identifying, in the image, a region of interest corresponding to at least one portion of the sample, which portion is poor in particles.

The liquid medium is then characterized on the basis of the region of interest thus identified.

Preferably, the sample is held by a fluid holder, the acoustic wave being applied by means of at least one electromechanical and in particular piezoelectric transducer that acts on said fluid holder so as to propagate the acoustic wave in the sample.

In a preferred embodiment, the acoustic wave applied to the sample is a stationary wave.

The method may have any one of the following features, whether independently or in combination:
- the sample may be held by a fluid holder, the acoustic wave being applied by means of an electromechanical and in particular piezoelectric transducer that acts on said fluid holder so as to propagate the acoustic wave in said sample. The fluid holder may be a fluidic chamber defining a thickness of the sample in a direction of propagation of the incident light wave;
- the acoustic wave applied to the sample may be a stationary wave;
- the sample may include a bodily fluid, in particular blood;
- the particles may be red blood cells.

The fluid holder may be a fluidic chamber that is configured to confine the sample between the light source and the photodetector. This fluidic chamber may in particular define a thickness of the sample, for example a constant thickness, in a direction of propagation of the incident light wave.

Another subject of the invention is a device for characterizing a sample, the sample including a liquid medium containing particles, the device including:
- a fluid holder that is configured to hold the sample;
- a light source that is arranged to emit an incident light wave that propagates towards the fluid holder that is configured to hold the sample;
- a photodetector that is configured to detect a light wave transmitted by the sample held by said fluid holder, when it is illuminated by the incident light wave;
- a processor that is able to characterize the sample depending on an intensity of the light wave detected by the photodetector.

The device also includes an electromechanical transducer that is configured to apply an acoustic wave that propagates in the sample held by the fluid holder, so as to separate, in the sample, a poor portion, said poor portion being poor in particles, and a rich portion, said rich portion being rich in particles, the processor being configured such as to characterize the liquid medium on the basis of the intensity of the light wave transmitted by the poor portion.

The electromechanical transducer may include a piezoelectric transducer or a plurality of piezoelectric transducers.

The electromechanical transducer may apply a pressure to said fluid holder, so as to form an acoustic wave in the sample held by the fluid holder.

According to an embodiment, the photodetector is an image sensor that is configured to acquire an image of the wave transmitted by the sample. The processor is configured to identify, in said image, a region of interest corresponding to at least one poor portion and to characterize the liquid medium on the basis of the region of interest thus identified.

According to a preferred embodiment, there are no magnifying optics between the image sensor and the fluid holder.

Other advantages and features will become more clearly apparent from the following description of particular embodiments of the invention, which embodiments are given by way of nonlimiting examples and shown in the figures listed below.

DETAILED DESCRIPTION OF THE ILLUSTRATED EMBODIMENTS

Figure 1A:
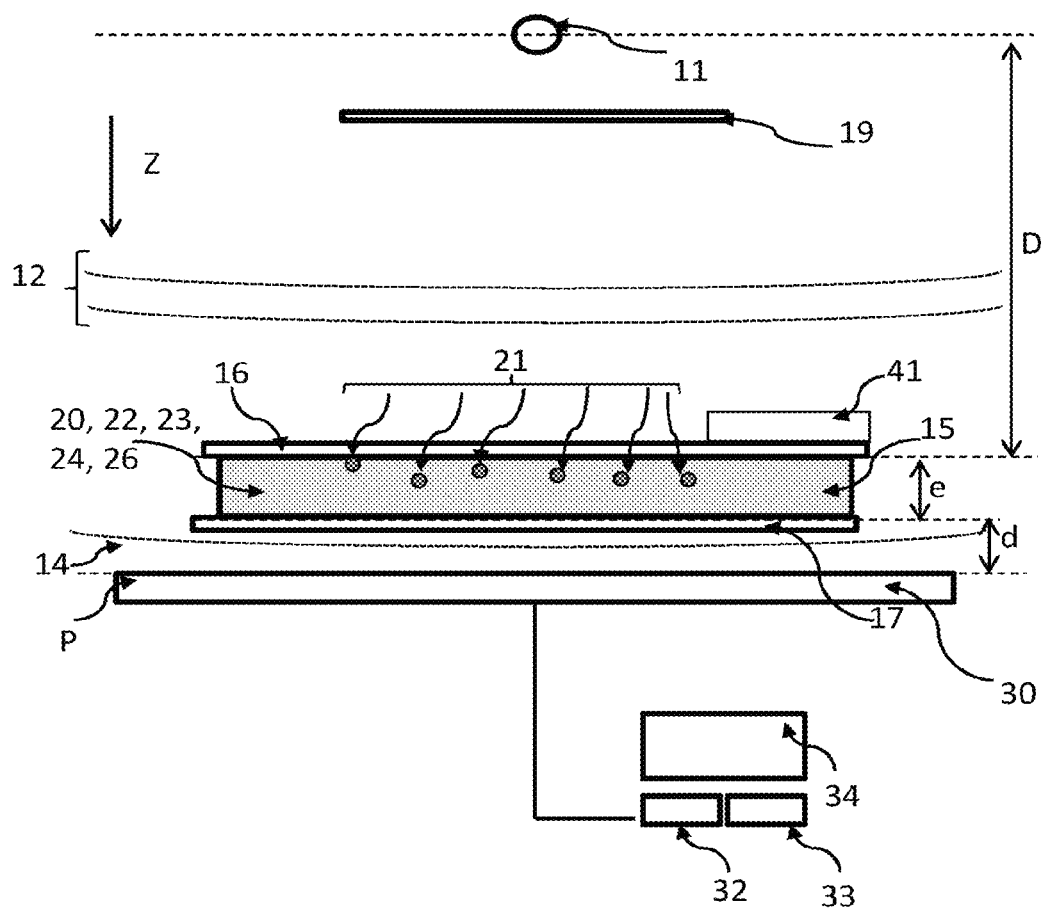
FIG. 1A shows a device according to one embodiment of the invention, illustrating a sample placed in a fluidic chamber coupled to a transducer, the transducer not being activated.
Figure 1B:
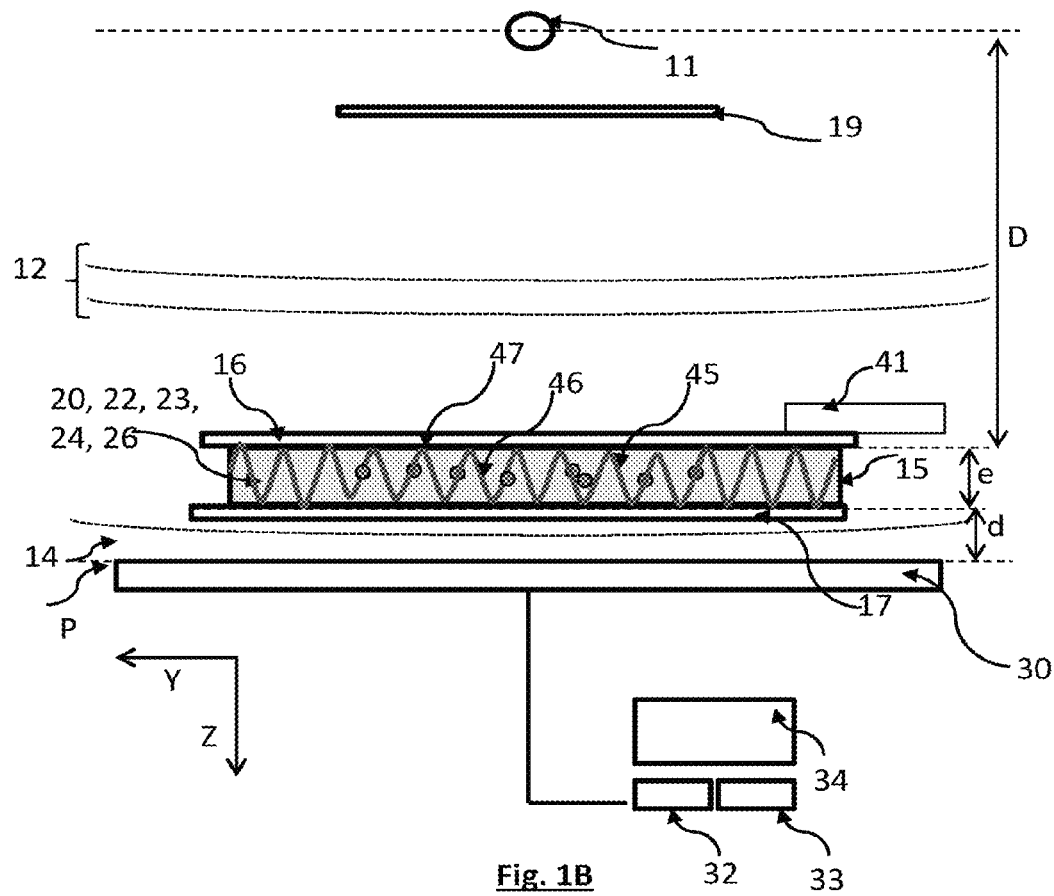
FIG. 1B illustrates a configuration similar to FIG. 1A, the transducer being activated. Comparison of FIGS. 1A and 1B will allow the technical effect associated with the activation of such a transducer to be understood.

FIG. 1A shows an example of the device 1 that is the subject of the invention. A light source 11 emits a light wave 12, called the incident light wave, in a spectral band of illumination, in the direction of a sample 20, along a propagation axis Z.

The sample 20 includes a liquid medium 22 and particles 21 contained in this liquid medium. The sample 20 may in particular comprise a bodily fluid, blood for example. It may in particular be a question of whole blood. The particles 21 may be blood particles, and more particularly red blood cells. It may also be a question of cells; microorganisms, bacteria or yeasts for example; microalgae; microspheres; or droplets that are insoluble in the liquid medium, lipid nanoparticles for example.

Preferably, the particles 21 have a diameter, or are inscribed in a diameter, smaller than 1 mm and preferably smaller than 100 μm. It is a question of microparticles (diameter smaller than 1 mm) or nanoparticles (diameter smaller than one μm). The liquid medium 22, in which the particles are contained, may be a liquid phase of a bodily fluid, a culture medium or a liquid sampled from the environment or from an industrial process.

The distance D between the light source 11 and the sample 20 is preferably larger than 1 cm. It is preferably comprised between 1 and 30 cm and typically 5 cm.

The light source 11 may be a light-emitting diode or a source of laser light such as a laser diode. The laser source 11 may include an optical filter 19, in particular a passband filter, allowing the spectral band of illumination of the incident light wave 12 to be adjusted. Such an optical filter is optional. The spectral band of illumination of the light wave emitted by the light source 11 is matched to an absorption spectrum of a coloured indicator 24 that is described in the description below.

The sample 20 is contained in a fluidic chamber 15. The fluidic chamber 15 is for example a microcuvette, commonly used in point-of-care type devices, and into which the sample 20 penetrates, for example by capillary action. In FIG. 1A, two longitudinal walls 16, 17 that are transparent, separated by a distance of 150 μm and designated by the terms upper wall and lower wall, respectively, have been shown. The distance between these two longitudinal walls 16, 17, along the propagation axis Z, corresponds to the thickness e of the sample. The latter typically varies between 20 μm and 1 cm, and is preferably comprised between 50 μm and 500 μm—for example it may be 150 μm. The lateral walls of the fluidic chamber, which extend parallelly to the axis of propagation Z, are not shown.

The fluidic chamber 15 is placed between the light source 11 and an image sensor 30 that is able to capture an image Im, called the transmission image, of a light wave 14 transmitted by the sample 20. The image sensor 30 lies in a detection plane P, preferably parallelly, or substantially parallelly to the longitudinal walls 16, 17 of the fluidic chamber 15. The term substantially parallelly means that the two elements in question may not be rigorously parallel, an angular tolerance of a few degrees, smaller than 20° or 10°, being acceptable.

The image sensor 30 includes a matrix array of CCD (charge-coupled device) or CMOS (complementary metal-oxide semiconductor) pixels. Image sensors the inter-pixel pitch of which is smaller than 3 μm are preferred because they allow images to be obtained with a satisfactory spatial resolution.

The absence of magnifying optics between the image sensor 30 and the sample 20 in this example will be noted. However this does not prevent focusing microlenses optionally being present level with each pixel of the image sensor 30. This allows an image Im, called the transmission image, of a light wave 14 transmitted by the sample to be formed while minimising the distance between the sample 20 and the image sensor 30. This allows a particularly simple and compact analysing device to be used. Thus, in the absence of magnifying optics, the distance d between the sample and the pixels of the photodetector is preferably smaller than 2 cm, or even than 1 cm, preferably comprised between 50 μm and 2 cm and preferably comprised between 100 μm and 2 mm.

A processor 32, for example a microprocessor, is able to process the images Im acquired by the image sensor 30. In particular, the processor is a microprocessor connected to a programmable memory 33 in which is stored a sequence of instructions allowing the image-processing and computational operations described in this description to be performed. The processor may be connected to a display screen 34.

The fluidic chamber 15 is mechanically connected to a first electromechanical transducer 41 that is activated to propagate an ultrasonic acoustic wave in the sample 20. The term ultrasonic designates the fact that the frequency of the acoustic wave is higher than 15 kHz and lower than 1 GHz. In this example, the first transducer 41 is a piezoelectric transducer that is able to vibrate one wall of the fluidic chamber 15, in the present case the upper wall 16, thereby causing an acoustic wave 45 to form at a frequency equal to the excitation frequency of the piezoelectric transducer, said acoustic wave propagating in the sample 20. The excitation frequency generally corresponds to a resonant frequency of the transducer 41, the operation of the latter being optimal at such a frequency. This resonant frequency depends on the transducer (the latter could also be termed a resonator). Generally, a piezoelectric transducer includes a piezoelectric material placed between two electrodes. Its resonant frequency depends on its shape and in particular on its thickness. The first transducer 41 may be placed in direct contact with the fluidic chamber 15, or placed on an interface element, the latter ensuring better coupling between the mechanical wave produced by the transducer and the acoustic wave formed in the sample 20.

The particles 21 in suspension in the sample 20 then find themselves placed in an acoustic pressure field, and experience a force, called the acoustic force, able to engender a movement of said particles. Depending on a parameter characterizing these particles, designated by the term acoustic contrast factor, the particles concentrate either in pressure nodes 46, i.e. in those zones of the sample in which the amplitude of the pressure wave is minimal, or in pressure antinodes 47, i.e. in those zones of the samples in which the amplitude of the pressure wave is maximal. Thus, use of an acoustic wave 45 allows the particles 21 to be concentrated in a way that depends on the pressure field formed in the sample and on the contrast factor of the particles. When the sample 20 includes blood particles, it has been observed that the red blood cells have a tendency to accumulate level with the pressure nodes 46. Use of an acoustic wave 45 thus allows the sample 20 to be segmented spatially into zones 20a that are poor in particles, so called depleted zones, and zones 20b that are rich in particles, so called enriched zones. The invention allows particles to be separated without moving the fluidic chamber 15 in which the sample is confined. In the sample, the particles 21 are not subjected to a rotary movement around a given axis of rotation, as in the centrifugation methods of the prior art.

Preferably, the acoustic wave 45 applied to the sample 20 is a stationary wave. In this case, the wavelength Λ of the acoustic wave 45 is advantageously set depending on the dimensions of the fluidic chamber 15. One condition may in particular be that a longitudinal dimension L, in which the acoustic wave propagates, is a multiple of the half wavelength. This condition, illustrated in FIG. 1D, is especially useful when said longitudinal dimension is small, typically about a wavelength Λ or of a few wavelengths. It is advantageous to form a stationary wave, because it makes it possible to ensure that the position of the pressure antinodes and pressure nodes obtained does not vary significantly over time. The longitudinal dimension L of the fluidic chamber may be larger than 10 times the wavelength λ, in which case it is possible to form a pseudo-stationary wave without precise adjustment of the wavelength with respect to this dimension. The term pseudo-stationary designates the fact that the wave includes a progressive component, but that the movement of the pressure antinodes 47 or pressure nodes 46 is sufficiently small for the movement of the particles 21, under the effect of this progressive component, to be negligible over the duration of acquisition, by the image sensor 30, of an image Im of the light wave 14 transmitted by the sample 20. The duration of such an acquisition is typically about 1 second, or is shorter than or equal to 1 second.

Figure 1C:
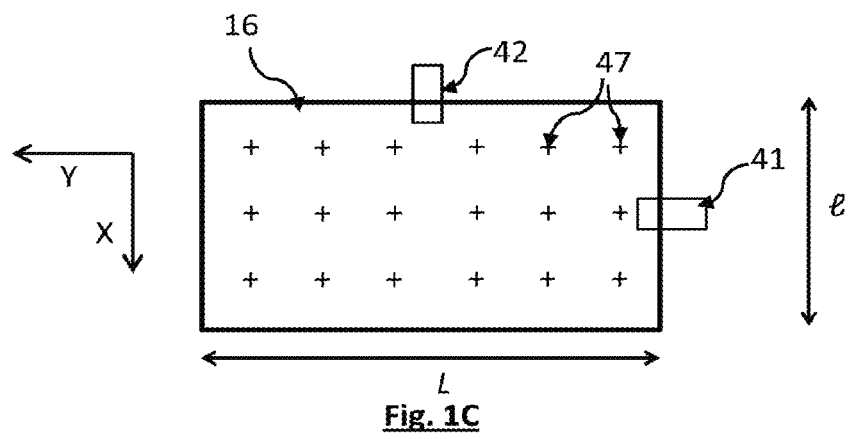
FIG. 1C shows an example of a fluidic chamber able to accommodate a sample.
Figure 1D:
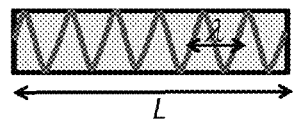
FIG. 1D schematically shows geometric conditions propitious to establishing a stationary pressure wave in a fluidic chamber.

FIG. 1C shows an embodiment in which the fluidic chamber is coupled to two transducers 41 and 42 that are oriented orthogonally to each other. A first transducer 41 is able to form a first acoustic wave moving along the axis Y, whereas a second transducer 42 is able to form a second acoustic wave moving along the axis X. This configuration allows a two-dimensional distribution of the pressure nodes and pressure antinodes to be obtained in the XY plane. FIG. 1C schematically shows a matrix-like distribution of the pressure antinodes 47 in the ideal case in which the first transducer 41 and the second transducer 42 respectively form a stationary wave of the same wavelength, this leading to a regular and two-dimensional distribution of the pressure antinodes 47.

Figure 2:
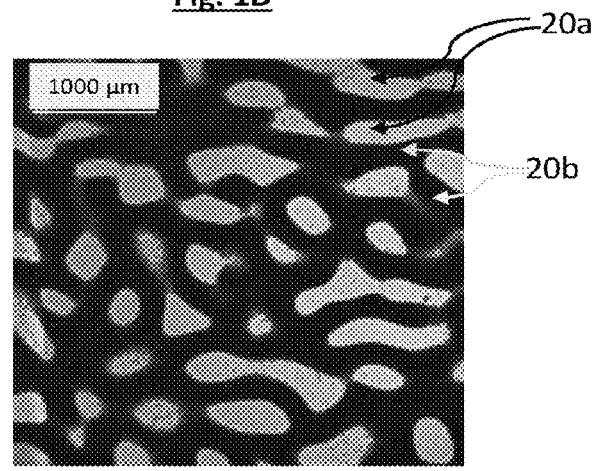
FIG. 2 shows an image produced with a device such as shown in FIG. 1B, the sample including blood diluted in a buffer.

FIG. 2 shows an experimental image of a first sample of a 80 μL volume including 46.8 μl of blood diluted in 33.2 μL of tris-glycine buffer. To obtain this image, the sample 20 was placed in a fluidic chamber 15 of parallelepipedal shape, of length L=2 cm, of width l=2 cm and of thickness e=150 μm. This fluidic chamber was placed 5 cm from a light source. The light source was a light-emitting diode emitting in a spectral band of emission centred on a wavelength of 660 nm. It was a light-emitting diode supplied by CoolLED under the reference pE illumination system 244 5100 red. It is preferable for the width of the spectral band of emission to be smaller than 100 nm, this width corresponding to a full-width at half maximum of the emission peak.

The fluidic chamber 15 included a transparent upper plate 16, made of glass and of 150 μm thickness. It also included a lower plate 17, made of glass and of 1 mm thickness. The lower plate was placed at a distance d of 1 cm from the image sensor 30, the latter being a CMOS sensor, the Hamamatsu digital camera C11440 22 CU.

The upper plate 16 was connected to two Noliac NCE 51 piezoelectric transducers that were oriented orthogonally to each other, as shown in FIG. 1C. Each transducer was supplied with an excitation signal the peak-to-trough voltage of which was 14 V, the phase of the excitation signal of the first transducer 41 and the phase of the excitation signal of the second transducer 42 being shifted by 90°. The resonant frequency of these transducers was 3 MHz. Firstly, taking into account the coupling between the transducers 41, 42 and said fluidic chamber, and the acoustic impedance of the sample 20, the resonant frequency of the fluidic chamber 15 was adjusted experimentally. This experiment was carried out using a calibration sample consisting of an aqueous solution containing polystyrene spheres of 40 μm diameter. It was observed, visually, that an optimal segmentation of the polystyrene spheres was obtained with an excitation signal frequency of 2.415 MHz.

Such an excitation frequency was applied to the transducers 41, 42 after the fluidic chamber 15 had been filled with the calibration sample described above. FIG. 2 shows an image obtained after activation of the transducers. Light regions 20a distributed with a two-dimensional distribution, and dark regions 20b may be seen. The dark regions corresponded to the pressure nodes, in which the particles concentrated to form the rich portions 20b. The incident light wave 12 was greatly attenuated by these particles, this explaining the low intensity of the wave 40 transmitted by the sample 20 level with these portions 20b that were dense in particles. In contrast, the light regions corresponded to the portions 20a of the sample that were poor in particles 21 because of the application of the acoustic wave 45. This image shows that under the effect of the acoustic wave 45, the optical transmission of the sample was no longer uniform: it was low in those enriched portions 20b of the sample which were rich in particles and high in the poor—or depleted—portions 20a By optical transmission, what is meant is a comparison between the intensity $i_{14}$ of the wave transmitted by the sample and the intensity $i_{12}$ of the wave incident on the sample. Optical transmission Tr is conventionally expressed in the form of a comparison, such a comparison in particular possibly taking the form of a ratio such as $$Tr = \frac{i_{14}}{i_{12}}.$$

Without application of the acoustic wave 45, the optical transmission of a sample is uniform, because of the uniform distribution of the particles. The application of the acoustic wave 45 allows a nonuniform spatial distribution in optical transmission to be obtained, the latter having minima level with the rich portions 20b and maxima level with the poor portions 20a. When the sample is blood, each poor portion is essentially composed of plasma and each rich portion is essentially composed of red blood cells. The application of the acoustic wave, in combination with detection of a light wave transmitted by the sample, level with a poor portion 20a, thus allows the optical transmission Tr of the plasma to be estimated.

Generally, and this is an essential point of the invention, the combination of an acoustic wave and of measurement of the intensity of the light wave transmitted by a sample allows an optical transmission of a zone that is poor in particles of the sample, or of a zone that is rich in particles of this sample, to be estimated.

The inventors have implemented the invention to carry out an assay of an analyte 26, and in particular of glucose, in blood. The principles of detection of glucose in a blood sample by implementation of enzymatic reactions leading to the formation of a coloured indicator are described in patents U.S. Pat. Nos. 3,964,974 and 5,866,349. Generally this colour-change method is based on:

oxidation of the glucose by NAD (acronym of nicotinamide adenine dinucleotide) acting by way of cofactor, in the presence of GDH (acronym of glucose dehydrogenase), leading to the formation of NADH+H$^+$ (acronym of nicotinamide adenine dinucleotide dihydride acid); reduction of a tetrazolium salt by NADH+H$^+$ in the presence of diaphorase (dihydrolipoyl dehydrogenase), this reaction leading to the formation of a coloured indicator 24 the concentration of which is representative of the glucose concentration in the sample.

The tetrazolium salt used may be MTT, acronym for 3-(4,5-dimethylthiazol-2-yl)-2,5-diphenyltetrazolium bromide, in which case the colour indicator is formazan and violet in colour.

The term colour indicator designates a chemical species having a particular colour, and the formation of which in the sample is able to modify the absorption spectrum or transmission spectrum of the sample.

Furthermore, the method includes a step of mixing the sample 20 with a reagent 23, allowing a coloured indicator 24 to be formed by reaction with the analyte 26 present in the sample 20, this analyte being, in this example, glucose. The reagent 23 may include GDH, NAD, diaphorase and MTT.

The formation of the coloured indicator 24 representative of the analyte 26 leads to a decrease in the optical transmission of the sample, and in particular in the plasma, in a spectral band of absorption (or spectral band of colouration) of the coloured indicator. It is known that this spectral band extends between 370 and 700 nm, with an absorption maximum towards $\lambda=565$ nm. Thus, when a glucose assay is implemented, it is usual to determine the optical attenuation of the analysed sample at 660 nm, the attenuation increasing as the concentration of glucose increases. Attenuation Att designates the complement of the transmission, such that Att=1−Tr.

Figure 3A:
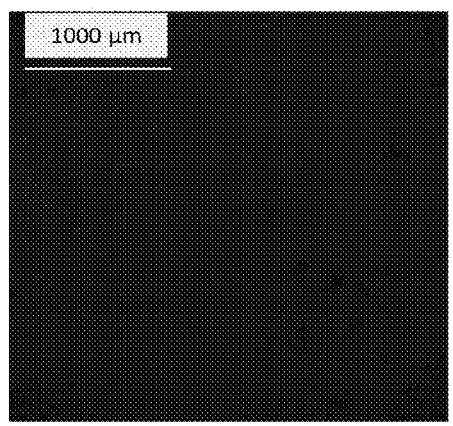
FIGS. 3A and 3B show images of what is called a reference sample with and without activation of transducers coupled to the fluidic chamber, respectively, the latter being similar to the example shown in FIG. 1C.
Figure 3B:
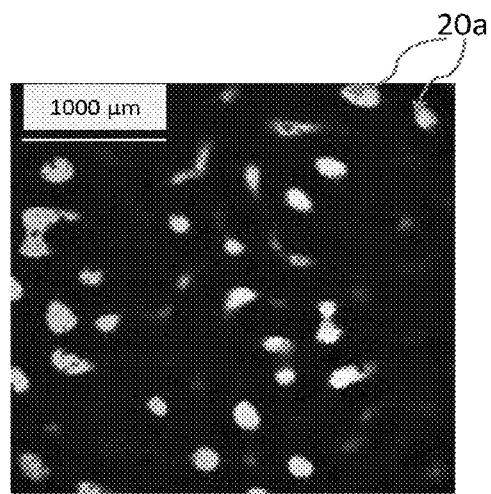

A reference sample was made up. This reference sample included 46.8 μL of blood, the concentration in glucose being 20 mmol, 20 μL of MTT and 13.2 μL of saline buffer. The reference sample contained neither cofactor (NAD) nor enzymes, in the present case GDH, allowing, under the effect of the glucose, the agent (NADH+H$^+$) responsible for the reduction of the MU into a coloured indicator to be formed. FIG. 3A shows an image of the reference sample 20 before activation of the transducers 41, 42. FIG. 3B shows an image of the reference sample after application of an acoustic wave, to the sample 20, by the transducers. Similarly to FIG. 2, the formation of light, poor regions 20*a* and dark, rich regions 20*b* was observed.

Next, images of a first and second test sample were taken, the samples being designated test$_1$ and test$_2$. Each test sample had the following composition:
blood: 46.8 μL;
MTT: 20 μL;
saline buffer 10 μL;
mutarotase: 0.8 μL;
GDH: 0.8 μL;
diaphorase: 0.8 μL;
NAD: 0.8 μL.

Figures 4A, 4B:
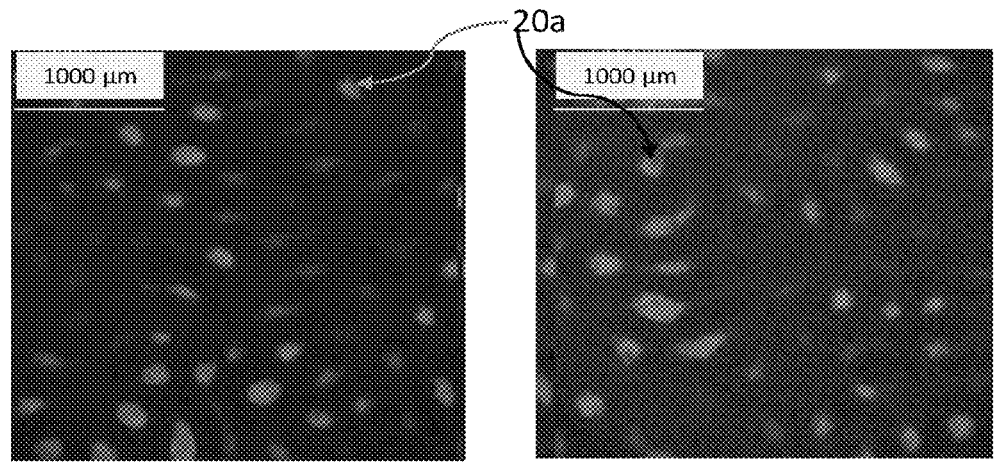
FIGS. 4A and 4B show respective images of two test samples during the assay of an amount of glucose, these images being obtained 109 seconds after activation of the piezoelectric transducers.

FIGS. 4A and 4B show the respective images of the first and second test samples, these images having being acquired 172 seconds and 175 seconds after addition of the reagent 23 allowing the coloured indicator 24 to be formed, respectively. A separation of the plasma and blood particles, essentially red blood cells, was observed, the light zones 20*a* allowing the optical transmission of the plasma to be determined. These images were repeated over time, at a rate of 1 image per second. The light zones 20*a* were observed to darken gradually, under the effect of the coloured indicator 24 formed by the enzymatic reactions described above.

The inventors quantified the variation in the intensity $i_{14}$ of the wave 14 transmitted by the reference sample ref and the two test samples test$_1$, test$_2$, while limiting the analysis of the acquired images to the regions of interest formed by the various portions 20*a* that were poor in particles.

Figure 5A:
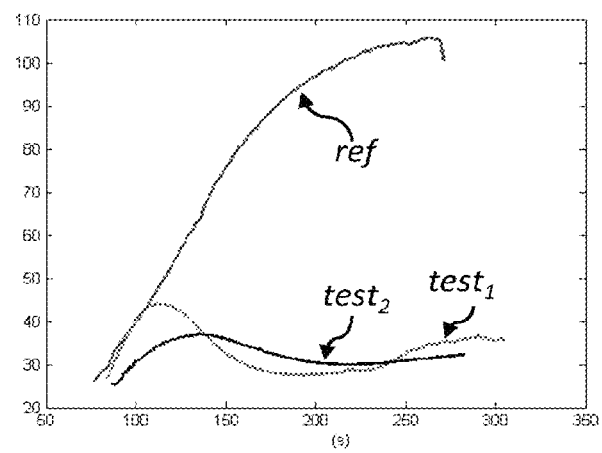
FIG. 5A shows the variation, as a function of time, of the average intensity of the poor portions of images of the reference sample and of two test samples.

To do this, the intensity of each of these images was thresholded, so as to exclude the various dark regions from the analysis, the latter regions being representative of the rich portions 20*b* of the sample 20. Thus, each thresholded image contained only light regions, corresponding to the poor portions 20*a*. In each thresholded image, the average intensity of the pixels of the various light zones was determined. FIG. 5A shows the variation, as a function of time, of the average intensity of the pixels in the light zones for the reference sample ref, the first test sample test$_1$ and the second test sample test$_2$, respectively. The unit of the x-axis is seconds, whereas the y-axis represents average intensity expressed in grey levels. For each test sample, the initial time, at the origin of the x-axis, corresponds to the addition of the reagent 23 allowing the enzymatic reaction leading to the formation of the coloured indicator 24 to be triggered. The curves were plotted from the time corresponding to the actuation of the transducers.

In the reference sample ref, the average intensity of the light zones increased then tended to stabilise, bearing witness to a gradual segmentation of the sample into light portions 20*a* and dark portions 20*b*.

In the two test samples, the average intensity increased, under the effect of the segmentation, then decreased and stabilized at comparable levels, because of the gradual formation of the coloured indicator, which tended to darken said poor portions 20*a*.

Figure 5B:
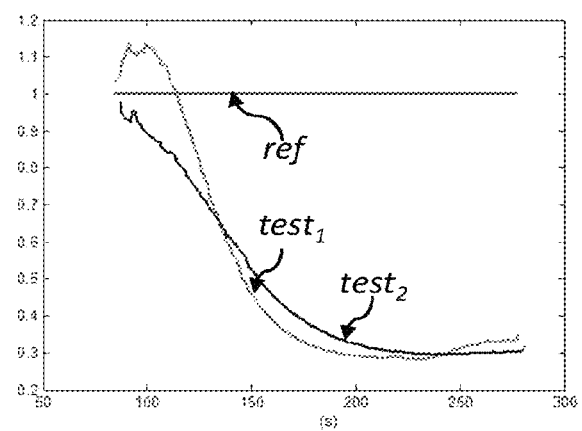
FIG. 5B shows the variation, as a function of time, of a ratio representative of the average intensity of the portions poor in particles of images of the reference sample and of two test samples to the average intensity of the portion poor in particles of the image of the reference sample, respectively.

For both the reference sample and the two test samples, the inventors normalized the intensity of each thresholded image by the average intensity, at the same time, of the thresholded image of the reference sample. The curve shown in FIG. 5B shows, for each sample, the variation, as a function of time, of the intensity of each thresholded image divided by the average intensity of the thresholded image of the reference sample. Assuming that the average intensity of the light zones of the reference image corresponds to the intensity of the incident wave, a quantity representative of the optical transmission of the plasma, i.e. of the liquid medium 22 in which the red blood cells are contained, as a function of time, is then obtained. It may be seen that this transmission was observed to decrease significantly and then to stabilize. Thus, on the basis of a calibration, carried out with test samples in which the amount of analyte is known, the invention allows an amount of analyte in an unknown sample to be estimated from the average intensity of the various light zones of its image.

The step of adding a reagent 23 able to modify an optical property of the sample depending on an amount of analyte 26 is optional. The invention may also be applied to the analysis of an optical property of one or more poor zones 20*a* of the sample, so as to characterize the liquid medium 22 in which the particles 21 are contained. When the sample is blood, the invention for example allows a pathological colouration of the plasma to be observed. In this case, the acoustic forces allow the sample to be segmented into poor portions 20*a* and rich portions 20*b*, as described above. The image sensor 30 allows an image Im representative of this segmentation to be viewed. From each light zone of the image, corresponding to a poor portion 20*a*, an optical property of the liquid medium 22 in which the particles 21 are contained, is estimated. It may be a question of determining the colour or determining an optical transmission or an optical absorption of the liquid medium 22. This method may comprise a step of comparing said estimated optical property with an optical property of a known reference sample, said optical property being determined beforehand in a calibration step.

One field to which the invention may be applied is that of the production of microalgae. The invention allows changes in the liquid medium in which the microalgae are contained to be tracked, for example a change in colour under the effect of chlorophyll extracted from said microalgae may be examined. The invention may also be applied to the culture of cells, to examine any variation in an optical property of the culture medium, for example under the effect of a variation in pH. The culture medium may then contain a coloured indicator the colour of which changes depending on the pH.

Figure 6A:
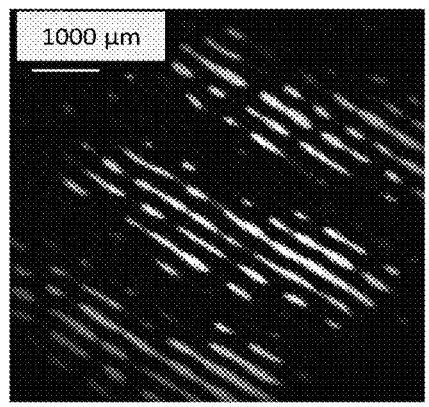
FIGS. 6A, 6B and 6C show images of three test samples having haematocrit levels respectively equal to 41%, 25% and 10%, respectively.
Figure 6B:
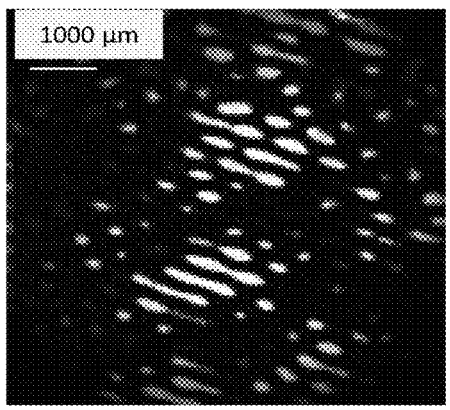
Figure 6C:
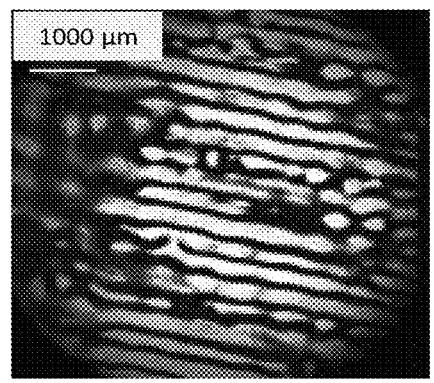

FIGS. 6A to 6C show images acquired by observing blood of varying haematocrit levels. The higher the haematocrit level, the greater the decrease in the area of poor portions 20a and the greater the increase in the area of rich portions 20b. In the images acquired by the image sensor 30, the higher the haematocrit level, the greater the decrease in the area of the light zones and the greater the increase in the area of the dark zones.

FIGS. 6A to 6C were obtained using three test samples $test_3$, $test_4$, $test_5$ that were obtained from human blood, in which samples the haematocrit level was equal to 41%, 25% and 10%, respectively. These samples were obtained by sampling blood from a human donor, the sampled blood having a haematocrit level of 41%. The haematocrit levels of 10% and 25% were obtained by diluting the blood in its own plasma, the latter having been extracted by centrifugation. FIGS. 6A to 6C were acquired by implementing a device similar to that described with regard to the evaluation of blood glucose level, a single piezoelectric transducer being used. The volume of each test sample was 90 µL.

Figure 7:
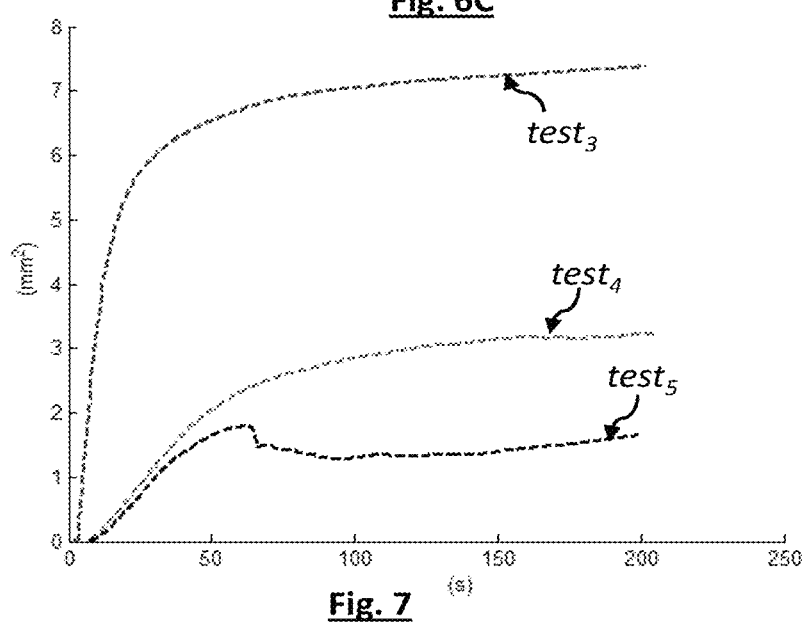
FIG. 7 shows the variation, as a function of time, of the cumulative area of the light areas of FIGS. 6A, 6B and 6C, these light areas representing the poor portions of the sample.

Images Im were obtained using the image sensor 30 described above. In each image Im acquired by the image sensor, a region of interest was selected in which the segmentation of the image into dark zones and light zones was stable over time. FIGS. 6A to 6C show this region of interest for the three samples in question, respectively. FIG. 7 shows, for each region of interest, the variation as a function of time of the cumulative area of the light zones, said cumulative area being expressed in $mm^2$. This cumulative area was representative of the poor zones 20a of each test sample. Just as for the preceding example, this cumulative area was obtained by thresholding intensity so as to exclude the various dark zones the intensity level of which was below a threshold. It may be seen, furthermore, that after a duration of about 65 seconds, the size of the cumulative area stabilized, this bearing witness to a certain stability in the segmentation of the particles.

Figure 8:
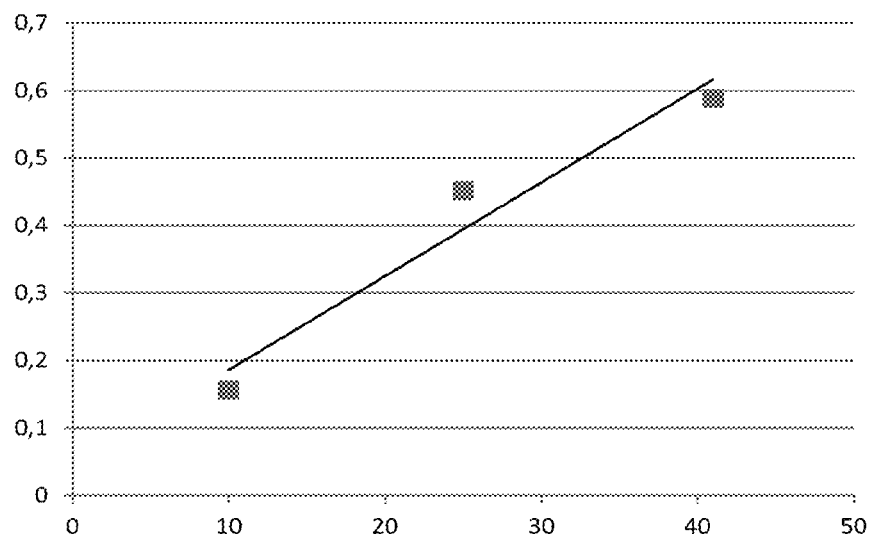
FIG. 8 is a calibration curve obtained in the trials presented with reference to FIGS. 6A, 6B, 6C and 7.

It may be seen that the higher the haematocrit level, the smaller the cumulative area of the light zones in the image. Thus, on the basis of a calibration using known test samples, the invention allows a haematocrit level to be determined by segmentation of the sample 20 into poor zones 20a and rich zones 20b, and by an observation of the representative area of these zones, or of a ratio between said zones. FIG. 8 shows a calibration curve obtained on the basis of the samples $test_3$, $test_4$, $test_5$, and allowing a haematocrit level (x-axis, the unit being %) to be estimated as a function of the inverse of the cumulative area of the poor zones 20a in a sample (y-axis, the unit being $mm^{-2}$). More generally, the invention allows an amount of particles 21 present in the liquid sample 20 to be estimated.

The invention may also be implemented by taking measurements of fluorescence. The incident light wave 12 may induce fluorescence of the sample 20, for example fluorescence of a fluorescent label present in the particles 21. An optical filter may be interposed between the sample and the image sensor 30, centred on a wavelength of fluorescence of the fluorescent label. The image acquired by the image sensor 30 allows the fluorescent particles to be quantified.

Thus, the invention allows a sample 20 containing particles 21 contained in a liquid medium 22 to be characterized, by:
estimating an amount of particles 21 in the sample;
determining an optical property, or its variation over time, of the liquid medium 22 in which the particles 21 are contained. When this optical property varies as a function of an analyte content, the invention allows the amount of said analyte in the sample to be determined.

In the preceding trials, an image sensor 30 was implemented, this being an advantageous configuration. Specifically, using such a sensor, the poor and rich portions may easily be identified and segmented by simple image processing methods. In addition, the acoustic wave 45 is not necessarily stationary and the invention is applicable, using an image sensor, when the spatial variation in the poor zones 20a and of the rich zones 20b is negligible with respect to the duration of acquisition of an image. However, the use of a photodetector that is not spatially resolved, a photodiode for example, is possible, but this assumes prior knowledge of the location of the rich zones 20b or the poor zones 20a, such that the photodetector is:
either optically coupled to a poor zone or to a rich zone;
or placed facing a poor zone or a rich zone.

This assumes that a stationary acoustic wave is formed and that the photodetector is located in a precise location with respect to said poor zones 20a or said rich zones 20b. Use of an image sensor is less constraining, it being possible to identify poor and rich zones in the images acquired by the sensor using conventional segmentation methods such as thresholding.

Figure 9:
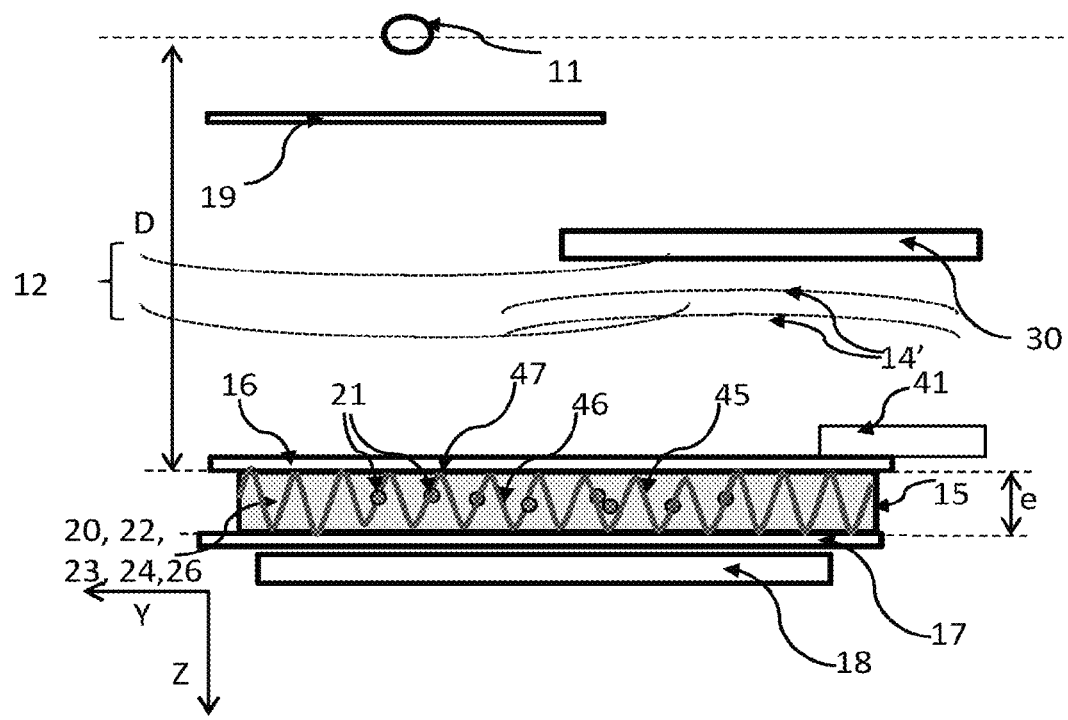
FIG. 9 illustrates another embodiment of the sample.

In one embodiment, which is shown in FIG. 9, the image sensor 30 is arranged in a reflection geometry, and not in transmission as in the embodiments described above. The image sensor 30 is able to form an image of a wave 14' transmitted by the sample, after having been reflected by a reflecting element 18. The latter may be a reflective holder on which the fluidic chamber 15 is placed, or a reflective deposit formed on the lower plate 17. The reflecting element 18 may be a white surface, a metallized surface or a mirror. The device 1' illustrated in FIG. 9 is a device in reflection.

In the examples described above, the sample was confined in a fluidic chamber 15. The invention also applies to a sample deposited on a fluid holder, the latter possibly simply being a transparent plate, the sample being deposited on this plate.

Apart from the assay of glucose in a blood sample, the invention will also possibly be applied to the assay of an analyte in a liquid containing particles, an advantageous segmentation of the liquid into at least one zone that is poor in particles and one zone that is rich in particles being implemented. The sample may in particular comprise a bodily fluid, the analyte possibly being glucose, cholesterol, or other elements such as proteins or cells.

Moreover, apart from the assay of an analyte, the invention will possibly be applied to other types of characterization of a sample, for example a characterization of a liquid medium 22 in which the particles 21 are in suspension, or an evaluation of an amount of said particles 21. The determination of a colour of blood plasma, of the colour of a cell or microalgae culture medium, and the estimation of a haematocrit level were given by way of example.

The invention is applicable to the characterization of bodily fluids, for the purpose of assisting with a diagnosis. However, the applications range beyond the field of bodily fluids and the invention will possibly be implemented to characterize liquid samples taken from the environment or concerning various industrial fields, for example, and non-exhaustively, the field of the culture of cells, the field of food processing and the field of the culture of microorganisms such as microalgae.

The invention claimed is:

1. A method for characterizing a sample, including a liquid medium containing particles, the method comprising the following steps:
   a) illuminating the sample using a light source that is able to emit an incident light wave that propagates towards the sample;
   b) detecting, using a photodetector, a light wave transmitted by the sample thus illuminated;
   c) characterizing the sample depending on a intensity of the light wave detected by the photodetector;
the method comprising, prior to step b), a step of applying an acoustic wave to the sample, said acoustic wave forming pressure nodes and pressure antinodes in the sample, so as to separate, in the sample, a poor portion, poor in particles, and a rich portion, rich in particles,
wherein step c) includes characterizing the liquid medium on the basis of the intensity of the light wave transmitted by the poor portion.

2. The method of claim 1, wherein the particles present in the sample concentrate, under the effect of said acoustic wave, either level with the pressure nodes, or level with the pressure antinodes.

3. The method of claim 1, wherein the characterization comprises estimating an amount of an analyte in the liquid medium.

4. The method of claim 1 including, prior to step b), mixing the sample with a reagent able to modify an optical property of the liquid medium under the effect of an analyte.

5. The method of claim 4, wherein the reagent forms a coloured indicator in the liquid medium, under the effect of the analyte.

6. The method of claim 5, wherein the sample includes cells in a cellular culture medium, the coloured indicator being such that its colour changes depending on the pH of the culture medium.

7. The method of claim 5, wherein the sample includes red blood cells in blood plasma, the coloured indicator being such that its colour changes depending on an amount of glucose in the plasma.

8. The method of claim 1, wherein the photodetector is an image sensor, such that:
   step b) comprises acquiring at least one image of the light wave transmitted by the sample;
   step c) comprises identifying, in the image, a region of interest corresponding to at least one poor portion of the sample;
the liquid medium being characterized on the basis of the region of interest thus identified.

9. The method of claim 1, wherein the sample is held by a fluid holder, the acoustic wave being applied by means of at least one electromechanical transducer that acts on said fluid holder so as to propagate the acoustic wave in the sample.

10. The method of claim 1, wherein the electromechanical transducer is a piezoelectric transducer.

11. The method of claim 1, wherein the acoustic wave applied to the sample is a stationary wave.

12. A device for characterizing a sample, the sample including a liquid medium containing particles, the device including:
   a fluid holder that is configured to hold the sample;
   a light source that is arranged to emit an incident light wave that propagates towards the fluid holder that is configured to hold the sample;
   a photodetector that is configured to detect a light wave transmitted by the sample held by said fluid holder, when it is illuminated by the incident light wave;
   a processor that is configured to characterize the sample depending on an intensity of the light wave detected by the photodetector;
wherein the device includes an electromechanical transducer that is configured to apply an acoustic wave that propagates in the sample held by the fluid holder, so as to separate, in the sample, a poor portion, poor in particles and a rich portion, rich in particles, the processor being configured such as to characterize the liquid medium on the basis of the intensity of the light wave transmitted by the poor portion.

13. The device of claim 12, wherein the electromechanical transducer includes a piezoelectric transducer or a plurality of piezoelectric transducers.

14. The device of claim 12, wherein the electromechanical transducer applies a pressure to said fluid holder, so as to form an acoustic wave in the sample held by the fluid holder.

15. The device of claim 12, wherein the photodetector is an image sensor that is configured to acquire an image of the wave transmitted by the sample, the processor being able to identify, in said image, a region of interest corresponding to at least one poor portion and to characterize the liquid medium on the basis of the region of interest thus identified.

16. The device of claim 15, wherein there are no magnifying optics between the image sensor and the fluid holder.

* * * * *